United States Patent [19]

Hallcher et al.

[11] Patent Number: 4,647,350

[45] Date of Patent: Mar. 3, 1987

[54] ELECTROLYTIC PREPARATION OF PERFLUOROALKANOIC ACIDS, PERFLUOROALKANOLS AND PERFLUOROALKYL ESTERS

[75] Inventors: Richard C. Hallcher, Maryland Heights; Zane V. Zeable, Olivette, both of Mo.

[73] Assignee: Monsanto Company, St. Louis, Mo.

[21] Appl. No.: 787,188

[22] Filed: Oct. 15, 1985

[51] Int. Cl.⁴ ............................................... C25B 3/04
[52] U.S. Cl. .................................................... 204/59 F
[58] Field of Search ...................................... 204/59 F

[56] References Cited

U.S. PATENT DOCUMENTS

| | | | |
|---|---|---|---|
| 2,713,593 | 7/1955 | Brice et al. | 204/59 F |
| 3,764,492 | 10/1973 | Balzer et al. | 204/59 R |
| 4,038,310 | 7/1977 | Björnson et al. | 204/59 F |
| 4,460,512 | 7/1984 | Millaver et al. | 204/59 F |

OTHER PUBLICATIONS

Ishikawa et al., "Ultrasound-Promoted Direct Carboxylation of Perfluoralkyl Iodides," Journal Fluorine Chemistry, 22(1983; 585–587).

Tyssee et al., "Some Cathodic Organic Synthesis Involving Carbon Dioxide," Tetrahedron Letters No. 47, pp. 4809–4812, 1972.

Calas et al., "Change in the Mechanism of the Electroreduction of Perfluoro-n-Hexyl Iodide," J. Electroanal. Chem., 89(1978) 363–372.

Blancou et al., "Preparation of Perfluoroalkane Carboxylic and Sulphonic Acid Derivatives", J.C.S. Chem. Comm, 1976, 885–886.

*Primary Examiner*—Terryence Chapman
*Attorney, Agent, or Firm*—Linda L. Lewis; James W. Williams, Jr.

[57] ABSTRACT

Perfluoroalkanoic acids and perfluoroalkanols are prepared by electrolysis of perfluoroalkyl chlorides in the presence of carbon dioxide or an aldehyde, for example, trifluoroacetic acid is obtained from chlorotrifluoromethane and carbon dioxide while trifluoroethanol is obtained from chlorotrifluoromethane and formaldehyde.

14 Claims, No Drawings

ELECTROLYTIC PREPARATION OF PERFLUOROALKANOIC ACIDS, PERFLUOROALKANOLS AND PERFLUOROALKYL ESTERS

The present invention relates to a process for preparing perfluoroalkanoic acids and perfluoroalkanols by electrolytic reduction of perfluroalkyl chlorides in the presence of carbon dioxide or an aldehyde.

BACKGROUND OF THE INVENTION

This invention concerns the preparation of fluorinated compounds that can be used as building blocks for fluorinated organics. For example, the trifluoromethyl group occurs in many biologically active compounds such as herbicides and biocides. Many new drugs are specifically functionalized fluorinated organics, such as flecainide acetate, a cardiac antiarrhymthmic agent.

Generally, prior procedures for preparing fluorinated compounds use hydrogen fluoride as the fluorinating agent in a halogen/fluorine exchange. Often, this step occurs late in a synthetic sequence and the desired selectivity is not always obtained. Methods which use other fluorinated precursors may be selective but the cost of the reagent is usually prohibitively high for commercial preparation. Trifluoroacetic acid and trifluoroethanol are reagents which are expensive as building block precursors.

The present invention specifically relates to the generation of trifluoroethanol and trifluoroacetic acid from trifluoromethyl chloride. Trifluoromethyl chloride is an inexpensive starting material as it is a by-product from dichlorodifluoromethane manufacture.

Procedures are known for carboxylation of some perfluoroalkyl iodides. Blaneou et al., J.C.S. Chem. Comm., Vol. 1976, pp 885-886 (1976) prepared perfluorobutanoic, perfluorohexanoic and perfluorooctanoic acids using reaction with carbon dioxide in a Zn-Cu dispersion. Percentage yields, however, were moderate, ranging from 40%-63%.

Ishikawa et al, J. Fluorine Chem., Vol. 22, pp. 585-587 (1983), similarly used chemical means to carboxylate perfluoroalkyl iodides. The reaction, using the n-octyl, n-hexyl, n-butyl and i-propyl perfluoroiodide, were ultrasound-promoted in the presence of zinc powder. Percentage yields of acid ranged from 48-77%. Calas et al., J. Electroanal. Chem. Vol. 89, pp. 363-372 (1978), prepared perfluorohexanoic acid by electroreduction of perfluoro-n-hexyl iodide, using a mercury electrode and lithium chloride as the supporting electrolyte in dimethylformamide, and bubbling in carbon dioxide. Yields over 90% were reported, but with some uncertainty noted. Carboxylation was found to depend strongly on the supporting electrolyte used. For example, no electrocarboxylation occurred when lithium perchlorate was used. Alkyl chlorides are generally recognized as having lower reactivities than alkyl iodides and alkyl bromides, (see e.g. Fieser and Fieser, Advanced Organic Chemistry, p. 341 (1961)). Moreover, trifluoromethyl chloride, in contrast to trifluoromethyl iodide, is a low boiling gaseous material which is poorly soluble in solvents such as dimethyl formamide.

Baizer et al (Tetrahedron Let., No. 47, pp 4809-4812, (1972)) reported production of esters, carbonates, mercuric compounds and oxalates from the reduction of alkyl halides and carbon dioxide at a mercury electrode. With n-pentylchloride, small amounts of pentyl hexanoate and bipentyl carbonate were reported, but with an oxalate as the major product. A related Baizer and Wagenknecht Pat. No. 3,764,492 similarly reports electrolysis results, principally at a mercury electrode. Substantial yields were apparently obtained with activated labile halide compounds, such as benzyl chloride and allyl chloride, but only a small amount of pentyl hexanoate identified by chromatographic analysis was reported for an example using 1-chloropentane, the only alkyl chloride example reported. In the Baizer work, esters produced, such as pentyl hexanoate from pentyl chloride, involved two molecules of alkyl halide reactant for each molecule of ester product. It is fortunate that a similar esterification reaction does not occur in the present process, at least to any great extent under the conditions utilized, as such an esterification would use up half of the expensive perfluoro reactant in forming an ester moiety. In the present process, an inexpensive agent, such as methyl chloride, serves very well as an esterifying agent. U.S. Pat. No. 3,764,492 further suggests that additional halide groups in the reactant may result in the production of polyesters.

SUMMARY OF THE INVENTION

The present invention relates to an electrolytic preparation of trifluoroalkanoic acids and trifluoroalkyl alcohols in which perfluoroalkylchlorides undergo electrolysis in the presence of carbon dioxide or an aldehyde. In particular, trifluoromethyl chloride and carbon dioxide can be readily electrolyzed in an aprotic solvent containing electrolyte salt to produce trifluoroacetic acid. The trifluoroacetic acid can be produced with high selectivity and with little or no formation of trifluoromethyl trifluoroacetate or oxalates. Trifluoromethyl chloride and formaldehyde can be electrolyzed under the same condition to produce trifluoroethanol. The substitution of other aldehydes for formaldehyde gives corresponding alkyltrifluoromethylcarbinols.

DETAILED DESCRIPTION OF THE INVENTION

The reaction of the present invention involves electrolysis of perfluoroalkyl chlorides in the presence of carbon dioxide or an aldehyde. If carbon dioxide is used, a carboxylation reaction occurs and the perfluoroalkanoic anion is formed which may be converted either to the free acid or to one of its esters. If formaldehyde is used as the carbon-oxygen source, the perfluoroalkyl alcohol is produced.

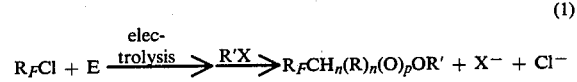

$$R_FCl + E \xrightarrow{\text{electrolysis}} R'X \longrightarrow R_FCH_n(R)_n(O)_pOR' + X^- + Cl^- \quad (1)$$

in which $R_F$ is a perfluoroalkyl group in which there can be any number of carbon atoms, e.g. perfluoromethyl, perfluoroethyl, perfluorohexyl, perfluorooctyl, and all valence positions of the carbon atoms are occupied by fluorine atoms; in which $R_FCl$ is a perfluoroalkyl chloride; in which E is either carbon dioxide or alkanal; in which R is hydrogen or an alkyl group; in which R' is a hydrogen or alkyl group, where the alkyl group can be any alkyl group, e.g. methyl, ethyl, propyl, benzyl, but for practical purposes will generally have no more than 10 carbon atoms; in which X represents halide or an acid anion; in which n is equal to either zero or one and p is equal to zero or one. If p=0, then n is 1. If p=1, then n is 0. The perfluoroalkyl chlorides of practical interest herein will generally contain up to 10 or so carbon atoms, and often less than 6 carbon atoms. Because either carbon dioxide or an aldehyde such as formaldehyde may be used as reactant, a possible mechanism suggests that the perfluoroalkyl chloride is reduced first to form the perfluoroalkylanion. The scheme can be pictured:

$$R_FCl + 2e^- \rightarrow R_F^- + Cl^- \quad (2)$$

$$R_F^- + CO_2 \rightarrow R_FCO_2^- \quad (3)$$

or $$R_F^- + H_2CO \rightarrow R_FCH_2O^- \quad (4)$$

but the reaction is part of the present invention regardless of what the actual mechanism may be. The carboxylate anion produced in reaction (3) may be acidified with any strong acid, e.g. hydrochloric acid, to yield the free carboxylic acid or be alkylated by any appropriate alkylating agent, such as alkyl halides, e.g., methyl iodide, ethyl iodide, to yield an ester.

Reaction (1) is of particular interest with trifluoromethyl chloride as the starting perfluoroalkylchloride; the reaction may be illustrated:

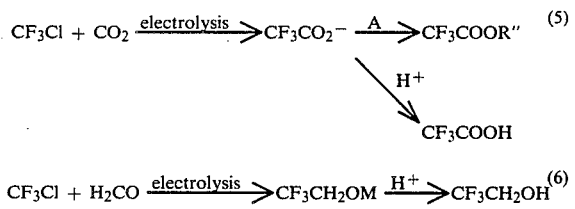

where A may be any appropriate alkylating agent, as described previously, to form the ester. For example, if ethyl iodide is used as the alkylating agent the resulting ester is ethyl trifluoroacetate. If the free acid is desired, acidification with any strong acid will yield trifluoroacetic acid. The reaction of trifluoromethyl chloride with formaldehyde yields a trifluoroethoxide which is readily converted to trifluoroethanol. The M in equation (6) represents a cation, such as a metal salt cation or quaternary ammonium cation.

Other aldehydes will react similarly to formaldehyde to produce perfluoroalkyl carbinols,

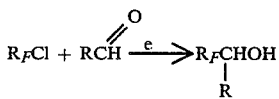

which in the case of chlorotrifluoromethane as reactant, are trifluoromethyl carbinols. In general, any aldehydes are suitable for the reaction, with those alkanols with 1 to 10 or so carbon atoms being convenient for use, e.g. acetaldehyde, propionaldehyde, butyraldehyde, 1-decanol, etc. The aldehydes are generally fairly soluble in the electrolysis solvents and sufficiently concentrated solutions for efficient operation can be readily obtained. Concentrations of about 1% to 2% by weight are sufficient for formaldehyde or other lower aldehydes and higher concentrations, up to the limit of solubility or higher can be employed. With higher aldehydes, it will be appropriate to use concentrations on a molar basis equivalent to or greater than 1 to 2% or so carbon dioxide by weight. In contrast to formaldehyde, the other aldehydes are generally readily available in monomeric form. Generally the amounts of aldehyde employed will be in the range of about 1 to about 20% or so by weight.

The electrolysis is carried out by passing an electric current through a medium which contains the perfluoroalkyl chloride in contact with the cathode in the presence of carbon dioxide or an aldehyde. The medium must have sufficient conductivity to conduct the electrolysis current. The required conductivity is generally achieved by employing common supporting electrolytes, such as electrolyte salts along with a liquid aprotic solvent having at least a moderately high dielectric constant ($\epsilon = 20$ to 50). However, any combination of electrolyte and aprotic solvent which permits the desired conductivity and solution of the perfluoro reactant may be employed. If the perfluoro reactant is a gaseous material, e.g. trifluoromethylchloride, and is only slightly soluble in the chosen solvent, dissolution may be effected by using a pressurized electrolytic cell.

In the present process an aprotic solvent with at least a medium dielectric constant is desirable in order to lower electrical resistance. Of course, the choice and concentration of electrolyte salt can also be used to lower electrical resistance. The solvents desirable herein include dimethylformamide, acetonitrile, propionitrile and benzonitrile.

In the present process it is desirable to use dry materials and to operate under nearly anhydrous conditions, as water can cause undesirable side reactions.

A supporting electrolyte is generally used to enhance conductivity. A supporting electrolyte is an electrolyte capable of carrying current but which will not interfere with the desired electrolysis reaction. Because the desired reaction in the present invention occurs at the cathode, electrolytes employed will generally have cations of more negative cathodic discharge potential than the discharge potential of the perfluoroalkyl chloride used.

In general, any supporting electrolyte salts can be utilized in effecting the present process, with due consideration to having conditions suitable for the discharge of the perfluoroalkyl chloride involved. The term salt is employed in its generally recognized sense to indicate a compound composed of a cation and an anion, such as produced by reaction of an acid with a base. The salts can be organic, or inorganic, or mixtures of such, and composed of simple cations and anions, or very large complex cations and anions. Amine and quaternary ammonium salts are generally suitable for use herein, as such salts generally have very negative discharge potentials.

Among the quaternary ammonium salts useful, are the tetralkyl ammonium, e.g. tetraethyl or tetrabutyl ammonium, methyltriethylammonium, etc., heterocyclic and aralkyl ammonium salts, e.g. benzyltrimethylammonium, etc. Various anions can be used with the foregoing and other cations, e.g. organic and inorganic anions, such as phosphates, halides, sulfates, sulfonates, alkylsulfates, tetrafluoroborate. It will be desirable to have some material present which is capable of a non-interfering discharge at the anode, such as some portion of a halide salt, in order that current can be carried without producing interfering contaminants. However, after initial electrolysis the chloride ion liberated from the perfluoroalkyl chloride can migrate to the anode and be discharged there and most salt anions will not thereafter be subject to discharge at the anode.

The concentration of the salts used may vary up to the maximum solubility of the salt in the electrolysis medium, but suitable concentrations will generally be in the range of about 0.2 to 0.6 molar. Because of some loss of salt noted above, the electrolyte salt should be replenished to maintain appropriate concentrations. In continuous processes, concentration can be maintained at a constant value.

Because many perfluoroalkyl chlorides are gaseous materials, e.g. trifluoromethyl chloride, trifluoroethyl chloride, and are not generally soluble in most aprotic solvents, they will desirably be maintained under pressure to provide appropriate concentrations. Pressures in the range of about 520 kPa to about 690 kPa are suitable, but higher pressures can be used, although possibly causing additional equipment costs.

If the reactants are gaseous materials, the present electrolysis can advantageously be conducted in an electrochemical cell capable of containing moderate pressures of about 100 to 150 psi, or so (689 to 1034 kPa or so). Such a cell comprises a stainless steel reactor body with a head capable of being sealed, a glass liner to resist the action of electrolytes and to prevent electrical contact with the metal outside wall, and a cathode and anode, which are electrically connected to sources of electric current. Relatively low pressure can also be used, such as down to 50 kPa or lower, but as the concentration of trifluorochloromethane maintained in the electrolysis medium declines, the process becomes less practical for commercial scale production purposes. Current densities in commercial electroorganic synthesis processes are generally in the range of about 10 to about 100 amperes per square decimeter, and it would be desirable to be in or approaching this range in the present invention. However, the present invention can be operated suitably at much lower current densities, such as in the range of about 1 to about 10 amperes/$dm^2$, particularly on a laboratory scale. Thus, it will generally be desirable to have the concentration of perfluoroalkyl chloride sufficient to maintain a current density of at least 1 ampere/$dm^2$, and preferably higher current densities such as 5 to 10 amperes/$dm^2$. In terms of concentration, it is desirable that the concentration of $CF_3Cl$ in the electrolysis medium be at least about 1 to 20% or so by weight for efficient operation. The pressure of $CF_3Cl$ in the reactor can conveniently be maintained at about 350 kPa to about 700 kPa, but some of the advantages of operation under pressure can be obtained at $CF_3Cl$ pressures of about 70 to 175 kPa or so. Thus, pressures in the range of about 70 to about 700 kPa or higher can usefully be employed. Carbon dioxide has considerable solubility in some of the useful aprotic solvents, so when $CO_2$ is the reactant, less $CO_2$ pressure is needed to obtain appropriate concentrations than is the case with $CF_3Cl$. However, it is important for good selectivity to have sufficient carbon dioxide present to react with intermediates produced from the $CF_3Cl$ or other perfluoroalkyl chloride, and this can be insured when using pressure apparatus, by operating under moderately elevated carbon dioxide pressures, such as 25 kPa or higher, such as in the ranges described above for $CF_3Cl$. It will generally be desirable to have $CO_2$ concentrations of at least about 1% to 2% or more by weight in the electrolysis medium. However, if desired, the carbon dioxide can be bubbled into the medium, at a suitable rate without operation under carbon dioxide pressure. While the carbon dioxide can readily be supplied in sufficient amount, if the concentration should be depleted, the intermediate anions apparently produced from the perfluoroalkyl chlorides can take part in carbene formation and ensuing reactions, with a loss of selectivity to desired products. Accordingly, the carbon dioxide will preferably be supplied at a rate to provide concentrations at least sufficient for needs at the current density employed, and this can conveniently be insured by operating under moderate carbon dioxide pressure.

When an aldehyde such as formaldehyde is a reactant, it is generally sufficiently soluble in the electrolysis medium for use without maintaining it under pressure. The formaldehyde can be supplied from usual sources and any sources which provide formaldehyde or an equivalent for reaction can suitably be employed, provided that compounds that would unduly interfere with the desired reaction are not introduced. Thus sources containing a high proportion of water will generally be avoided, but formaldehyde, paraformaldehyde, methylal and the various acetals, hemiacetals and polymers of formaldehyde can be used. When paraformaldehyde is employed, the use of moderately elevated temperatures, such as about 50° to about 100° C. or so, contributes to reaction rate by causing depolymerization of the formaldehyde.

For the present electrolysis, the anode can be any electrode material so long as it is relatively inert under the reaction conditions. Ordinarily, the anode will have little or no influence on the course of the electrolysis, and can be selected so as to minimize expense and any corrosion problem. Generally, graphite is suitable. The cathode can be selected from suitable materials including mercury, lead or graphite. Lead and graphite have ease of handling compared to the liquid mercury. For continuous processes, lead, graphite or other solid metals would be most suitable.

In the persent process, a divided cell will ordinarily be employed, i.e., some separator will be used to prevent free flow of reactants and products between cathode and anode. Generally the separator is some mechanical barrier which is relatively inert to electrolyte materials, e.g., sintered glass, porous ceramic or an ion exchange membrane. A permselective membrane designed to permit selective passage of cations is particularly advantageous to prevent the acid anion produced from migrating to the anode, for example, a Nafion ® permselective membrane of sulfonated fluoropolymer. In a divided cell, it is possible to employ the same or different medium in the cathode and anode sides. Ordinarily, the same electrolyte and solvent are used in both chambers. An undivided cell can be utilized but interfering reactions detract from efficiency and tend to make such operations impractical for production purposes.

In an undivided cell, the halogen generated at the anode can migrate to the cathode to be reduced, thereby utilizing current in a non-productive manner and eventually causing a radical decline in the desired reaction. This problem can possibly be avoided by changing conditions or electrolyte salts so that carbon dioxide or other harmless products are generated at the anode. So far as the initial reactants are concerned, there is no special problem in permitting chlorotrifluoromethane, carbon dioxide or formaldehyde to contact the anode, although the desirable reactions generally occur near the cathode. In fact when operating under pressure, it may be convenient equipment-wise, to have the chlorotrifluoromethane and carbon dioxide pressures be the same in the cathode and anode chambers.

It will be desirable to employ high current densities in order to achieve high use of electrolytic cell capacity, and therefore, for production purposes it will generally be desirable to use as high a density as feasible with the equipment employed. A spinning disk electrode is convenient for achieving a fairly high current density in laboratory demonstration cells.

The present electrolysis can be conducted at ambient temperatures but reaction temperatures as high as 90° to 95° C. or higher may be used.

The electrolysis cells described in the procedural examples herein are primarily for laboratory demonstration purposes. Production cells are usually designed with a view to the economics of the process, and characteristically have large electrode surfaces, usually consisting of solid metals, and short distances between electrodes. The present process is best suited to a continuous flow operation. Continuous operations can involve recirculation of electrolyte and recycling of unused reactants after separation of product. Additional reactants can be added continuously or intermittently; electrolyte salt can be augmented or replenished.

When carbon dioxide is the reactant, the resulting product may be either the free perfluoroalkanoic acid or one of its esters. After electrolysis, a strong acid, such as hydrochloric acid, may be added to the catholyte to obtain the free acid. If an ester product is desired, an alkylating agent, such as an alkyl halide, such as ethyl iodide or methyl chloride, may be added. In continuous operation, the alkylating agent can be added to the product stream.

The product obtained in the present process can be recovered by a variety of procedures. Gas chromatographic or gas chromatographic-mass spectral analysis has been largely used for convenient separation and identification in the procedural examples herein. However, for production purposes, a separation by distillation is convenient. The gaseous $CF_3Cl$ and $CO_2$ can be readily removed in a small stripper for recycle to the electrolysis cell. The catholyte can then be treated with dry HCl or an alkylating agent to form trifluoroacetic acid or its ester. The acid or ester can be readily distilled from the catholyte, which can then be recycled to the electrolysis cell. Thus, the process can be conveniently operated in a continuous mode with separation of product and recycle of reactants and electrolysis medium.

EXAMPLE 1

A 450 ml glass-lined Parr pressure "mini-reactor" was modified to contain electrodes. The cathode consisted of a lead foil on the surface of a graphite spinning disk, threaded on to a stirrer shaft which also provided the electrical connection for the cathode. All other surfaces of the disk were insulated. The effective electrode surface of the disk was about 32 cm². The anode was graphite felt which was stationary in the bottom of the reactor cell. The cathode compartment consisted of a polyethylene cylinder with a Nafion ®-423 salt-form ion exchange membrane acting as the bottom of the cylinder and as the cell divider. The cathode chamber sat above the stationary anode. A polyethylene mesh was used to keep the cathode chamber from the anode. Stirring of the anolyte was effected with a magnetic stirrer. The cathode and anode chambers have separate valved intake tubes for charging and gas sampling through the head of the reactor.

The anolyte, consisting of 100 ml of 0.6M tetrabutylammonium iodide in dry dimethylformamide (dried on a column of alumina, activity grade 1), and catholyte, consisting of 50 ml of 0.6M tetrabutyl ammonium iodide in dry dimethylformamide, were charged through their respective sampling valves. The reactor cell was pressurized to 520 kPa with dry carbon dioxide and the pressure was then increased to 1035 kPa with trifluoromethyl chloride. Stirring was started in both compartments and a constant current of 300 mA was maintained for three hours. At the end of the reaction time, the trifluoroacetate in the catholyte was alkylated with 10 g of ethyl iodide to give ethyl trifluoroacetate. The current efficiency of product formation was 84% based on gas chromatographic analysis.

EXAMPLE 2

The same rotating disk, pressurized cell was utilized as in Example 1. The anolyte consisting of 100 ml of 0.6M tetrabutylammonium iodide in dry dimethylformamide, and the catholyte, consisting of 3.8 g of paraformaldehyde and 50 ml of 0.6M tetrabutylammonium iodide in dry dimethylformamide, were charged through their respective sampling valves. The reactor cell was pressurized with trifluoromethyl chloride to 690 kPa. Stirring was started in both compartments. A constant current of 100 mA was maintained for one and one-half hours after raising the reactor temperature to about 90° C. Gas chromatographic-mass spectral analysis confirmed the trifluoroethanol as the major product. The current efficiency of product formation was 72%.

EXAMPLE 3

A divided cell pressure vessel made of glass-lined stainless steel tubing similar to that described in Example 1 was utilized. Mercury was used as the cathode. The mercury pool was placed in the bottom of the reactor cell. The pool covered a platinum wire electrical lead and was stirred with a magnetic stirring bar. The anode was surrounded by an alundum thimble of coarse porosity which had been treated with a Nafion ® ion exchange membrane resin, as the cell divider. The anode cup was charged with 30 ml of 0.4M tetrabutyl ammonium iodide in dry dimethylformamide. The catholyte consisted of 50 ml of 0.4M tetrabutylammonium iodide in dry dimethylformamide. The reactor cell was pressurized to 345 kPa with dry carbon dioxide and then to 1035 kPa with trifluoromethyl chloride. Stirring was commenced. A constant current of 80 mA was maintained for 6 hrs. At the end of the reaction time, the catholyte was alkylated with 5.0 g of ethyl iodide. The current efficiency of ethyl trifluoroacetate product formation was 75% based on gas chromatographic analysis.

EXAMPLE 4

The same reactor cell as in Example 3 was utilized except a lead electrode was used as the cathode. The catholyte consisted of 50 ml of 0.4M tetrabutylammonium tetrafluoroborate in dry dimethylformamide. The anolyte consisted of 30 ml of the same solution. The reactor cell was pressurized to 345 kPa with dry carbon dioxide, then the pressure was increased to 1035 kPa with trifluoromethyl chloride. Stirring was commenced. A constant current of 80 mA was maintained for 6 hrs. At the end of the reaction time, 5.0 g of ethyl iodide was added to the catholyte. The current efficiency of product formation was 66% based on gas chromatographic analysis.

EXAMPLE 5

The same reactor cell as in Example 3 was utilized except a graphite electrode was used as the cathode and a medium porosity alundum thimble which had been treated with a Nafion ® 1100 EW ion exchange resin. The catholyte consisted of 50 ml of tetrabutyl ammonium tetrafluoroacete in dry dimethylformamide. The anolyte consisted of 30 ml of the same solution to which 14.6 grams of tetrabutylammonium iodide was added. The reactor cell was pressurized to 345 kPa with dry carbon dioxide, then increased to 1035 kPa with trifluoromethyl chloride. Stirring was commenced. A constant current of 80 mA was maintained for 6 hours. At the end of the reaction time, 5.0 of ethyl iodide was added to the catholyte. The current efficiency of product formation was 53% based on gas chromatographic analysis.

We claim:

1. A process of converting perfluoroalkyl chlorides to perfluoroalkanoic acids or perfluoroalkyl alcohols which comprises electrolyzing the perfluoroalkyl chloride in the presence of an electrophile selected from carbon dioxide or an aldehyde under conditions to effect reduction and the production of a corresponding acid or alcohol.

2. The process of claim 1 in which the process is represented:

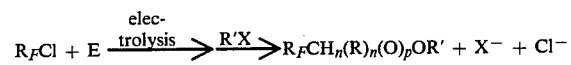

where
$R_F$ = perfluoroalkyl with up to 10 carbon atoms
E = carbon dioxide or alkanal with up to 10 carbon atoms
R = hydrogen or an alkyl group with up to 9 carbon atoms
R' = hydrogen or alkyl with up to 10 carbon atoms
X = halide
p = 0 or 1
n = 0 if p = 1
n = 1 if p = 0.

3. The process of claim 1 in which trifluoromethyl chloride is converted to trifluoroacetic acid or its ester.

4. The process of claim 1 in which trifluoromethyl chloride is converted to trifluoroethanol.

5. The process of claim 1 in which the electrophile is carbon dioxide.

6. The process of claim 1 in which the electrophile is formaldehyde.

7. The process of claim 1 in which the process is represented:

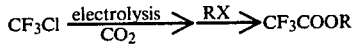

where
R = hydrogen or alkyl with up to 10 carbon atoms and
X = Cl, I or Br.

8. The process of claim 1 in which the process is represented:

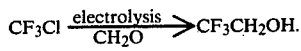

9. The process of claim 1 in which the electrolysis is carried out in an aprotic solvent selected from dimethylformamide, acetonitrile, propionitrile or benzonitrile.

10. The process of claim 1 in which electrolysis is conducted in a supporting electrolyte which is a quaternary ammonium salt.

11. The process of claim 1 in the electrolysis is conducted at a cathode selected from lead, mercury or graphite.

12. The process of claim 1 in which a spinning disk is employed as a cathode in the process.

13. A process of producing ethyl trifluoroacetate which comprises electrolyzing trifluoromethyl chloride in the presence of dry carbon dioxide and a catholyte solution comprising tetrabutylammonium iodide in dimethylformamide at a total pressure of 1035 kPa for about three hours and alkylating the catholyte product with ethyl iodide to form the ethyl trifluoroacetate product.

14. A process of producing trifluoroethanol which comprises electrolyzing trifluoromethyl chloride in the presence of paraformaldehyde and a catholyte comprising tetrabutylammonium iodide in dimethylformamide under a total pressure of 690 kPa for about 1.5 hours to form the trifluoroethanol product.

* * * * *